United States Patent [19]

Nagahara et al.

[11] Patent Number: 4,606,860
[45] Date of Patent: Aug. 19, 1986

[54] RHODANINES USEFUL AS A THERAPEUTIC AGENT FOR DIABETIC COMPLICATIONS

[75] Inventors: Michiko Nagahara, Shiga; Yoshitaka Ohishi, Uji; Motoyuki Yajima, Otsu; Katsumi Nogimori, Otsu; Shigeki Kurokawa, Otsu; Norio Kajikawa, Kyoto, all of Japan

[73] Assignee: Kaken Pharmaceutical Co., Ltd., Tokyo, Japan

[21] Appl. No.: 675,580

[22] Filed: Nov. 28, 1984

[30] Foreign Application Priority Data

Aug. 24, 1984 [JP] Japan .................. 59-177210

[51] Int. Cl.$^4$ .................. C07D 421/04; A61K 31/33
[52] U.S. Cl. .................. 548/183; 540/575; 544/133; 544/230; 544/367; 546/209
[58] Field of Search .................. 544/367; 548/183; 514/255, 369, 218, 230; 260/245.5

[56] References Cited

U.S. PATENT DOCUMENTS 4,446,143  5/1984  Tanouchi et al. .................. 546/135
4,464,382  8/1984  Tanouchi et al. .................. 548/183

FOREIGN PATENT DOCUMENTS 45165   2/1982  European Pat. Off. ............ 544/183
47109   3/1982  European Pat. Off. ............ 544/183
334806 12/1977  U.S.S.R. .................. 544/183

OTHER PUBLICATIONS

Tanouchi et al, Chem. Abst. 96-217830n.
Tanouchi et al, Chem. Abst. 97-23781x.
Mousseron, Chem. Abst. 72-121519w.
Duerr, Chem. Abst. 77-15623u.
Boehringer, Chem. Abst. 80-47977r.
Pollock, Chem. Abst. 94-84108k.
Sukla et al, Chem. Abst. 97-216065a.
Pathak et al, Chem. Abst. 97-92183r.

*Primary Examiner*—Donald G. Daus
*Assistant Examiner*—Cecilia Shen
*Attorney, Agent, or Firm*—Armstrong, Nikaido, Marmelstein & Kubovcik

[57] ABSTRACT

A rhodanine derivative having the following general formula (I):

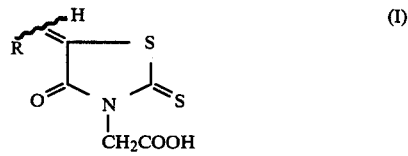

wherein R is a mono- or di-alkylamino group having 1 to 6 carbon atoms which may be substituted by a hydroxyl group; an alkenylamino group having 3 to 6 carbon atoms; a phenylamino group, the benzene ring of which may be substituted by a lower alkyl group, a lower alkoxyl group, phenyl group or a halogen atom; or a cyclic amino group which may contain in the ring an oxygen atom or a nitrogen atom to which a lower alkyl group is attached; or a nontoxic salt thereof. The rhodanine derivative has potent platelet aggregation inhibiting activity and aldose reductase inhibiting activity and therefore is useful as a therapeutic agent for diabetic complications.

2 Claims, No Drawings

RHODANINES USEFUL AS A THERAPEUTIC AGENT FOR DIABETIC COMPLICATIONS

BACKGROUND OF THE INVENTION

The present invention relates to novel rhodanine derivatives, processes for preparing the same and a pharmaceutical composition containing the same as a therapeutic agent for diabetic complications.

In recent years, westernization of eating habits has resulted in a marked increase in the number of diabetic patients and measures for the treatment thereof are urgently needed.

As therapeutic agents for diabetes, insulin and blood sugar lowering agents have so far been used widely. However, diabetes is not a mere disorder of sugar metabolism but a disease also involving a variety of complications and therefore the therapeutic effects of the above-mentioned agents alone are not enough for the treatment of diabetes.

Among main complications, cerebral and coronary vascular disturbances account for about 50% of causes of deaths resulting from diabetes [Y. Goto et al., Sogo Rinsho, 22, 779 to 785 (1973)].

Blood platelets play an important role in the development of such vascular disturbances. Thus, in a diabetic condition, platelets are in the state of hyperfunction, causing thrombosis and at the same time arteriosclerosis [H. Heath et al., Diabetologia, 7, 308 to 315 (1971)]. Therefore, platelet aggregation inhibitors are useful in the treatment of vascular disturbances such as mentioned above.

On the other hand, diseases of the eye, such as retinopathy and cataract, are also important diabetic complications and form the primary cause of blindness of the aged. In the development of such diseases, not only disturbance of retinal and other blood vessels, namely microangiopathy, is an important pathogenic factor, but also a certain kind of sugar metabolism disorder is concerned [K. H. Gabbay, Adv. Metab. Disord., 2(2), 424 (1973)]. Thus, in the diabetic condition, polyols such as sorbitol are accumulated to an extraordinary extent, causing osmotic pressure increase and water retention, which lead to ocular tissue disturbance. Therefore, inhibition of aldose reductase which is essential to polyol synthesis can possibly be effective in the prevention and treatment of the above-mentioned diseases of the eye [R. G. Judzewitsch et al., New Eng. J. Med., 308, 119 to 125 (1983); J. H. Kinoshita et al., Metabolism, 28 (1), 462 to 469 (1979)].

SUMMARY OF THE INVENTION

It is an object of the present invention to provide a novel compound useful as a therapeutic agent for diabetic complications including perceptual disorder, autonomic disturbance, diabetic nephropathy, and ocular diseases such as retinopathy and cataract.

This and other objects of the present invention will become apparent from the description hereinafter.

DETAILED DESCRIPTION

The present invention provides a rhodanine derivative having the following general formula (I):

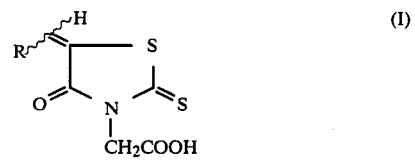

wherein R is a mono- or di-alkylamino group having 1 to 6 carbon atoms which may be substituted by a hydroxyl group; an alkenylamino group having 3 to 6 carbon atoms; a phenylamino group, the benzene ring of which may be substituted by a lower alkyl group, a lower alkoxyl group, phenyl group or a halogen atom; or a cyclic amino group which may contain in the ring an oxygen atom or a nitrogen atom to which a lower alkyl group is attached; and a nontoxic salt thereof.

Examples of the alkylamino group as the group R in the formula (I) are, for instance, methylamino, dimethylamino, 2-hydroxyethylamino, isobutylamino and hexylamino groups. Examples of the alkenylamino group as the group R in the formula (I), for instance, allylamino, butenylamino, pentenylamino and hexenylamino groups. The phenylamino group as the group R in the formula (I) may have on the benzene ring a lower alkyl group preferably having 1 to 4 carbon atoms, a lower alkoxyl group preferably having 1 to 4 carbon atoms, phenyl group or a halogen atom such as fluorine, chlorine, bromine or iodine. Examples of the phenylamino group are, for instance, 2-biphenylylamino, 3-methoxyphenylamino, 2-methoxyphenylamino, 3-chlorophenylamino, 4-bromophenylamino and m-tolylamino groups. The cyclic amino group as the group R in the formula (I) may contain in the ring an oxygen atom or a nitrogen atom to which a lower alkyl group preferably having 1 to 3 carbon atoms is attached, and preferably has a ring of 5 to 7 members. Examples of the cyclic amino group are morpholino, piperidino, 4-methylpiperazin-1-yl and 4-methylhomopiperazin-1-yl groups.

Examples of the nontoxic salts of the rhodanine derivative (I) are pharmaceutically acceptable salts, for instance, metal salts such as sodium salt, potassium salt, magnesium salt and calcium salt; salts with amine compounds represented by the general formula (III) mentioned below, such as methylamine, dimethylamine, ethanolamine, allylamine, isobutylamine, hexylamine, morpholine and methylpiperazine; mineral acid salts such as hydrochloride and sulfate.

The rhodanine derivative (I) includes any of trans form, cis form and mixture of these isomers.

The compounds represented by the general formula (I) and nontoxic salts thereof as provided by the present invention have potent platelet aggregation inhibiting activity which is comparable to that of Persantine (dipyridamole by generic name) which is an anti-platelet aggregation agent in widest use. At the same time, they have potent aldose reductase inhibiting activity and very low toxicity. Therefore, they can serve as excellent therapeutic agents for diabetic complications.

The preferred compounds among the compounds represented by the general formula (I) are shown in Table 1.

TABLE 1

| Compound No. | Formula | Name |
|---|---|---|
| 1 | CH₃NHCH=C(C(=O)-NCH₂COOH)-S-C(=S)-S (rhodanine ring) | 3-Carboxymethyl-5-methyl-aminomethylidenerhodanine |
| 2 | (CH₃)₂NCH=C(C(=O)-NCH₂COOH)-S-C(=S)-S | 3-Carboxymethyl-5-dimethyl-aminomethylidenerhodanine |
| 3 | HOCH₂CH₂NHCH=C(C(=O)-NCH₂COOH)-S-C(=S)-S | 3-Carboxymethyl-5-hydroxyethylaminomethylidenerhodanine |
| 4 | CH₂=CHCH₂NHCH=C(C(=O)-NCH₂COOH)-S-C(=S)-S | 3-Carboxymethyl-5-allylaminomethylidenerhodanine |
| 5 | (CH₃)₂CHCH₂NHCH=C(C(=O)-NCH₂COOH)-S-C(=S)-S | 3-Carboxymethyl-5-isobutyl-aminomethylidenerhodanine |
| 6 | CH₃CH₂CH₂CH₂CH₂CH₂NHCH=C(C(=O)-NCH₂COOH)-S-C(=S)-S | 3-Carboxymethyl-5-hexylaminomethylidenerhodanine |
| 7 | m-CH₃O-C₆H₄-NHCH=C(C(=O)-NCH₂COOH)-S-C(=S)-S | 3-Carboxymethyl-5-m-methoxyphenylaminomethylidenerhodanine |
| 8 | o-CH₃O-C₆H₄-NHCH=C(C(=O)-NCH₂COOH)-S-C(=S)-S | 3-Carboxymethyl-5-o-methoxyphenylaminomethylidenerhodanine |

TABLE 1-continued

| Compound No. | Formula | Name |
|---|---|---|
| 9 | (3-chlorophenyl)-NHCH=C(C(=O)-N(CH₂COOH)-C(=S)-S-) | 3-Carboxymethyl-5-m-chlorophenylaminomethylidene-rhodanine |
| 10 | (4-bromophenyl)-NHCH=C(C(=O)-N(CH₂COO)-C(=S)-S-) | 3-Carboxymethyl-5-p-bromophenylaminomethylidene-rhodanine |
| 11 | (3-methylphenyl)-NHCH=C(C(=O)-N(CH₂COOH)-C(=S)-S-) | 3-Carboxymethyl-5-m-methylphenylaminomethylidene-rhodanine |
| 12 | morpholino-N-CH=C(C(=O)-N(CH₂COOH)-C(=S)-S-) | 3-Carboxymethyl-5-morpholinomethylidenerhodanine |
| 13 | CH₃N(piperazine)N-CH=C(C(=O)-N(CH₂COOH)-C(=S)-S-) | 3-Carboxymethyl-5-N—methyl-piperazinomethylidene-rhodanine |
| 14 | CH₃N(homopiperazine)N-CH=C(C(=O)-N(CH₂COOH)-C(=S)-S-) | 3-Carboxymethyl-5-N—methyl-homopiperazinomethylidene-rhodanine |
| 15 | (2-biphenylyl)-NH-CH=C(C(=O)-N(CH₂COOH)-C(=S)-S-) | 3-Carboxymethyl-5-(2-biphenylyl)aminomethylidene-rhodanine |

Japanese Patent Application Kokai Tokkyo Koho Nos. 57-28074 and 57-4047, corresponding to U.S. Pat. Nos. 4,446,143 and 4,464,382 respectively, some rhodanine derivatives for use as reductase inhibitors. However, between the rhodanine derivatives described in the above-cited publications and the rhodanine derivatives of the invention, there is a substantial difference in the substituent at position 5. Moreover, the rhodanine derivatives of the invention have platelet aggregation inhibiting activity. The publications cited above mention nothing of such activity.

In addition, the rhodanine derivatives (I) and non-toxic salts thereof according to the present invention further contain a secondary or tertiary amine moiety in their molecule. The introduction of such amine moiety can increase the hydrophilic character and decrease the relative liposolubility, whereby the aldose reductase inhibiting activity in vivo can be prevented from decreasing as a result of protein binding and so forth [cf. Bird, A. E. and Marshall, A. C., Biochem. Pharmacol., 16, 2275 (1967); Scholtan, W., Arzneimttelforschung, 18, 505 (1968); Kitagawa, H., Noguchi, T. and Ito, R., Kusuri no Taisha (Drug Metabolism), page 87 (1971); Jusko, W. J. and Gretch, M., Drug metabolism Reviews, 5, 43 (1976)].

The rhodanine derivatives represented by the general formula (I) are prepared by reacting a 3carboxymethylrhodanine derivative having the following general formula (II):

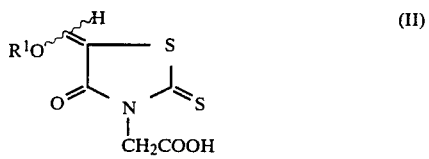

wherein $R^1$ is an lower alkyl group, or a salt thereof with an amine compound having the following general formula (III):

wherein $R^2$ is hydrogen atom or a lower alkyl group, and $R^3$ is an alkyl group having 1 to 6 carbon atoms which may be substituted by a hydroxyl group; an alkenyl group having 3 to 6 carbon atoms; phenyl group, the benzene ring of which may be substituted by a lower alkyl group, a lower alkoxyl group, phenyl group or a halogen atom; or $R^2$ and $R^3$ may be combined together with the nitrogen atom to which $R^2$ and $R^3$ attach to form a ring which may contain in the ring an oxygen atom or a nitrogen atom to which a lower alkyl group is attached.

In the above formula (II), the lower alkyl group represented by $R^1$ is preferably alkyl groups having 1 to 4 carbon atoms, such as methyl, ethyl, propyl and butyl groups.

In the above formula (III), the lower alkyl group represented by $R^2$ is preferably alkyl groups having 1 to 4 carbon atoms, such as methyl, ethyl, n-propyl, isopropyl, n-butyl and isobutyl groups. The group represented by $R^3$ is alkyl groups having 1 to 6 carbon atoms which may be substituted by a hydroxyl group, such as methyl, ethyl, n-propyl, isopropyl, n-butyl, isobutyl, n-pentyl, n-hexyl and 2-hydroxyethyl; alkenyl groups having 3 to 6 carbon atoms, such as allyl, butenyl, pentenyl and hexenyl groups; and phenyl groups which may be substituted by a lower alkyl group preferably having 1 to 4 carbon atoms such as methyl, ethyl, propyl or butyl group, a lower alkoxyl group preferably having 1 to 4 carbon atoms such as methoxy, ethoxy, propoxy or butoxy group, phenyl group, or a halogen atom such as fluorine, chlorine, bromine or iodine, for instance, 2-biphenylyl, 3-methoxyphenyl, 2-methoxyphenyl, 3-chlorophenyl, 4-bromophenyl and m-tolyl groups. Examples of the cyclic amine compound which $R^2$ and $R^3$ form together with the nitrogen atom to which $R^2$ and $R^3$ attach and may contain in the ring an oxygen atom or a nitrogen atom to which a lower alkyl group preferably having 1 to 3 carbon atoms such as methyl, ethyl or propyl group, is attached are morpholine, piperidine, N-methylpiperazine and N-methylhomopiperazine.

The reaction of the compound (II) with the amine compound (III) is conducted preferably in the following manner: The compound (II) is dissolved in a polar protic solvent including a lower alcohol such as methanol, ethanol or propanol, or a polar aprotic solvent such as acetone, dimethylformamide (hereinafter referred to as "DMF") or dimethyl sulfoxide (hereinafter referred to as "DMSO"). In dissolving the compound (II) in a solvent, the mixture may be heated somewhat. An amine compound (III) is added to the solution of the compound (II). The amount of the amine compound (III) used is preferably from 1 to 2.5 moles per 1 mole of the compound (II). The obtained mixture is agitated at a temperature of from room temprature to 90° C., preferably from 50° to 60° C., for 1 to 24 hours. After the reaction is completed, the reaction mixture is cooled to form a precipitate. The precipitate is separated by filtration and recrystallized from a solvent to give the rhodanine derivative (I). Examples of the solvent used are mixture of methanol and ether; mixture of ethyl acetate and petroleum ether; ethyl acetate; ethanol; mixture of acetone and petroleum ether; acetone; water; mixture of DMSO and water; and mixture of methanol, ethyl acetate and petroleum ether.

The compound (II) used as a starting material is prepared, for instance, by dissolving 3-carboxymethylrhodanine having the following formula (IV):

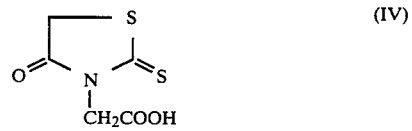

or its salt in a solvent such as acetic anhydride, adding to the solution ethyl orthformate in an amount of 1 to 2 moles per 1 mole of the compound (IV), agitating the resultant under reflux for 1 to 5 hours to effect the reaction, concentrating the reaction mixture, and purifying the resulting residue in a usual manner such as recrystallization or silica gel column chromatography.

The rhodanine derivatives and nontoxic salts thereof according to the invention are useful in the prevention or treatment of diabetic complications such as diseases of circulatory organs due to their excellent platelet aggregation inhibiting activity, and also useful in the prevention or treatment of nervous disturbance resulting from abnormal accumulation of polyols, diabetic retinopathy and cataract due to their excellent aldose reductase inhibiting activity. The effect on such prevention and treatment can be sufficiently exhibited by the dosage of about 0.05 to about 200 mg/day to adult.

The rhodanine derivatives (I) and nontoxic salt thereof can be formulated into pharmaceutical compositons in the form of tablets, capsules, injections, powders, pills, granules, suppositories and eye drops. Such preparations can be prepared in a usual manner using conventional pharmaceutically acceptable carries. Examples of the carrier are, for instance, excipients, binders, diluents and lubricants. Typical examples thereof are lactose, starch, sugar, microcrystalline cellulose, magnesium stearate, silicon dioxide, talc, physiological salt solution and sterilized water.

The present invention is more specifically described and explained by means of the following Examples. It is to be understood that the present invention is not limited to the Examples, and various change and modifications may be made in the invention without departing from the spirit and scope thereof.

The abbreviations in the Examples mean the followings:
MP: Melting point
EA: Elementary analysis
IR: Infrared absorption spectrum ($\nu_{max}^{KBr}$ cm$^{-1}$)
MS: Mass spectrum (20 eV, Direct)
NMR: Proton nuclear magnetic resonance spectrum (in DMSO-d$_6$, δ(ppm))

REFERENCE EXAMPLE

[3-Carboxymethyl-5-ethoxymethylidenerhodanine]

A mixture of 36 g (0.189 mole) of 3-carboxymethylrhodanine, 33.6 g (0.225 mole) of ethyl orthoformate and 225 ml of acetic anhydride was subjected to reaction under reflux for about 1 to 2 hours and then the reaction mixture was concentrated. A precipitate was formed by the addition of a small amount of chloroform to the residue. The precipitate was separated and recrystallized from ethyl acetate to give 29.2 g of 3-carboxymethyl-5-ethoxymethylidenerhodanine in the form of brownish white crystal (yield: 62.5 %).

The characteristic properties of the product are as follows:
MP: 190° to 192° C.
IR (cm$^{-1}$): 3100 to 2900 (CH), 2600 to 2400 (COOH), 1730 (ring C=O), 1680 (COOH)
MS (m/e): 247 (M$^+$), 219 (M$^+$—C$_2$H$_4$)
NMR (ppm): 1.25 (3H, t, —CH$_3$), 4.15 (2H, q, —CH—), 4.40 (2H, s, —CH$_2$COO—), 7.60 (1H, s, —CH=)

EXAMPLE 1

[3-Carboxymethyl-5-methylaminomethylidenerhodanine (Compound No. 1)]

A mixture of 0.68 g (0.010 mole) of methylamine hydrochloride and 5 ml of ethanol, which was neutralized with 1.0 g (0.010 mole) of triethanolamine, was added to a mixture of 1.2 g (0.005 mole) of 3-carboxymethyl-5ethoxymethylidenerhodanine and 10 ml of ethanol. The reaction was conducted at a temperature of 50° to 60° C. for 1 hour. The reaction mixture was concentrated and the resulting residue was recrystallized from ethanol to give 1.0 g of 3-carboxymethyl-5-methylaminomethylidenerhodanine methylamine salt (yield: 79.2 %).

The salt was dissolved into water and the resulting solution was made neutral or weekly acidic with a dilute hydrochloric acid. The formed precipitate was separated by filtration and recrystallized from a mixture of methanol, ethyl acetate and petroleum ether (5/3/1 by volume) to give 0.56 g of 3-carboxymethyl-5-methylaminomethylidenerhodamine in the form of brown powdered crystal (yield: 46.7 %).

The characteristic properties of the product are as follows:
MP: 247° to 249° C. (decomposition)
IR (cm$^{-1}$) 3300 to 2850 (NH, CH), 2700 to 2450 (COOH), 1730 (ring C=O), 1690 (COOH)
MS (m/e): 232 (M$^+$), 188 (M$^+$—COO)
NMR (ppm):

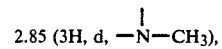
2.85 (3H, d, —N—CH$_3$), 4.3 (2H, s, —CH$_2$COO—), 7.25 (1H, d, —CH=), 7.90 (1H, d, —NH—)
EA: shown in Table 2

EXAMPLE 2

[3-Carboxymethyl-5-dimethylaminomethylidenerhodanine (Compound No. 2)]

The same procedures as in Example 1 except that dimethylamine hydrochloride was used instead of methylamine hydrochloride were repeated to give 3-carboxymethyl-5-dimethylaminomethylidenerhodanine in the form of reddish brown crystal (yield: 73.3 %).

The characteristic properties of the product are as follows:
MP: 202° to 204° C. (decomposition)
IR (cm$^{-1}$): 3250 to 2800 (CH), 2650 to 2400 (COOH), 1730 (ring C=O), 1680 (COOH)
MS (m/e): 246 (M$^+$)
NMR (ppm):

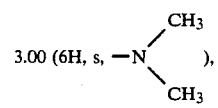
3.00 (6H, s, —N(CH$_3$)$_2$), 4.30 (2H, s, —CH$_2$COO—), 7.30 (1H, s, —CH=)
EA: shown in Table 2

EXAMPLE 3

[Ethanolamine salt of 3-Carboxymethyl-5-hydroxyethylaminomethylidenerhodanine (Compound No. 3)]

0.62 Gram of monoethanolamine was added to a mixture of 1.2 g (0.005 mole) of 3-carboxymethyl-5ethoxymethylidenerhodanine and 10 ml of ethanol. The reaction was carried out at a temperature of 50° to 60° C. for 1 hour. The formed precipitate was separated by filtration and recrystallized from a mixture of methanol and ether (7/3 by volume) to give 0.85 g of 3-carboxymethyl-5-hydroxyethylaminomethylidenerhodanine ethanolamine salt in the form of light brown crystal (yield: 53.1 %).

The characteristic properties of the product are as follows:
MP: 170° to 172° C. (decomposition)
IR (cm$^{-1}$): 3400 to 2800 (OH NH, CH) 2600 to 2400 (COOH), 1700 (ring C=O)
NMR (ppm): 2.95 (2H, t, —CH$_2$NH$_2$), 3.2 to 3.7 (6H, m,m HOCH$_2$CH$_2$NH—, HOCH$_2$CH$_2$NH$_2$), 4.25 (2H, s, —CH$_2$COO—), 7.4 (1H, s, —CH=)
EA: shown in Table 2

EXAMPLE 4

[3-Carboxymethyl-5allylaminomethylidenerhodanine (Compound No. 4)]

0.3 Gram (0.005 mole) of allylamine was added to a mixture of 1.2 g (0.005 mole) of 3-carboxymethyl-5-ethoxymethylidenerhodanine and 10 ml of ethanol, and the resulting mixture was subjected to reaction at a temperature of 50° to 60° C. for 1 hour. The reaction mixture was cooled and the formed precipitate was separated by filtration and recrystalized from a mixture of methanol and ether (7/3 by volume) to give 0.68 g of 3-carboxymethyl-5-allylaminomethylidenerhodanine in the form of yellow crystal (yield: 52.6%).

The characteristic properties of the product are as follows:
MP: 170° to 172° C. (decomposition)
IR (cm$^{-1}$): 3300 to 2850 (NH, CH), 2600 to 2400 (COOH), 1730 (ring C=O), 1685 (COOH)
MS (m/e): 258 (M$^+$)
NMR (ppm):

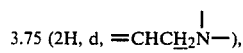

3.75 (2H, d, =CHC$\underline{H}$$_2$N—), 4.23 (2H, s, —CH$_2$COO—), 5.00 (2H, d, CH$_2$=), 5.43 to 5.70 (1H, m, CH$_2$=CHCH$_2$—), 7.30 (1H, s, —CH=)
EA: shown in Table 2

EXAMPLE 5

[3-Carboxymethyl-5-isobutylaminomethylidenerhodanine (Compound No. 5)]

0.74 Gram (0.01 mole) of isobutylamine was added to a mixture of 1.2 g (0.005 mole) of 3-carboxymethyl-5-ethoxymethylidenerhodanine and 10 ml of ethanol, and the resulting mixture was subjected to reaction at a temperature of 50° to 60° C. for 1 hour. The reaction mixture was concentrated and the resulting residue was dried and dissolved into water. The solution was made neutral or weakly acidic with a dilute hydrochloric acid and the formed precipitate was separated by filtration. The precipitate was washed with water, dried and recrystallized from a mixture of ethyl acetate and petroleum ether (4/1 by volume) to give 0.9 g of 3-carboxymethyl-5-isobutylaminomethylidenerhodanine in the form of yellowish red crystal (yield: 64.3%).

The characteristic properties of the product are as follows:
MP: 174° to 176° C. (decomposition)
IR (cm$^{-1}$) 3300 to 2850 (NH, CH), 2650 to 2450 (COOH), 1720 (ring C=O), 1680 (COOH)
MS (m/e); 274 (M$^+$), 230 (M$^+$—COO)
NMR (ppm):

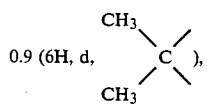

0.9 (6H, d, 1.40 to 1.85 (1H, m, >CH—), 2.95 (2H, t, —CHNH—), 4.23 (2H, s, —CH$_2$COO—), 7.20 (1H, d, —CH=), 8.00 (1H, d, —NH—)
EA: shown in Table 2

Example 6

[3-Carboxymethyl-5-hexylaminomethylidenerhodanine (Compound No. 6)]

The same procedures as in Example 5 except that hexylamine was used instead of isobutylamine were repeated to give hexylamine salt of 3-carboxymethyl-5hexylaminomethylidenerhodanine in the form of yellow crystal by recrystallization from ethyl acetate.

The characteristic properties of the product are as follows:
MP: 139° to 141° C. (decomposition)
NMR (ppm): 0.90 (6H, t, (—CH$_3$) X 2), 1.00 to 1.60 (16H, m, (—CH$_2$—) X 8), 2.60 (2H, t, NH$_2$CH$_2$CH$_2$—), 3.15 (2H, t, —NHCH$_2$CH$_2$—), 4.10 (2H, s, —CH$_2$COO—), 7.18 (1H, s, —CH=)

The above salt was dissolved into water and the resulting solution was treated in the same manner as in Example 5. The obtained product was recrystallized from a mixture of ethyl acetate and petroleum ether (4/1 by volume) to give 0.9 g of 3-carboxymethyl-5-hexylaminomethylidenerhodanine in the form of yellow crystal (yield: 60%).

The characteristic properties of the product are as follows:
MP: 243° to 245° C. (decomposition)
IR (cm$^{-1}$) 3300 to 2850 (NH, CH), 2600 to 2400 (COOH), 1710 (ring C=O), 1690 (COOH)
MS (m/e): 302 (M$^+$)
NMR (ppm): 0.85 (3H, t, CH$_3$—), 1.1 to 1.6 (8H, m, (—CH$_2$—) X 4), 3.0 to 3.3 (2H, m, —NHCH$_2$CH$_2$—), 4.23 (2H, s, —CH$_2$COO—), 7.3 (1H, s, —CH=), 7.8 to 8.2 (1H, broad, —NH—)
EA: shown in Table 2

Example 7

[3-Carboxymethyl-5-m-methoxyphenylaminomethylidene-rhodanine (Compound No. 7)]

The same procedures as in Example 4 except that m-anisidine was used instead of allylamine were repeated to give 1.1 g of 3-carboxymethyl-5-m-methoxyphenylaminomethylidenerhodanien by recrystallization from ethanol in the form of yellow crystal (yield: 68.8 %).

The characteristic properties of the product are as follows:
MP: 240° to 242° C. (decomposition)
IR (cm$^{-1}$): 3350 to 2800 (NH, CH), 2700 to 2500 (COOH), 1740 (ring C=O), 1680 (COOH)
MS (m/e): 324 (M$^+$)
NMR (ppm): 3.58 (3H, s, —OCH$_3$), 4.40 (2H, s, —CH$_2$COO—), 6.20 to 6.97 (4H, m, aromatic proton), 7.65 (1H, d, —CH=), 9.8 (1H, d, —NH—)
EA: shown in Table 2

EXAMPLE 8

[3-Carboxymethyl-5-o-methoxyphenylaminomethylidenerhodanine (Compound No. 8)]

The same procedures as in Example 4 except that o-anisidine was used instead of allylamine and the reaction was conducted at a room temperature for 4 hours were repeated to give 1.0 g of 3-carboxymethyl-5-o-methoxyphenylaminomethylidenerhodanine in the form of yellow fine needle by recrystallization from ethanol (yield: 62.5 %).

The characteristic properties of the product are as follows:
MP: 244° to 246° C. (decomposition)
IR (cm$^{-1}$) 3300 to 2850 (NH, CH), 2700 to 2450 (COOH), 1720 (ring C=O), 1675 (COOH)
MS (m/e): 324 (M$^+$)
NMR (ppm): 3.60 (3H, s, —OCH$_3$), 4.36 (2H, s, —CH$_2$COO—), 6.50 to 7.10 (4H, m, aromatic proton), 7.55 (1H, d, —CH=), 9.58 (1H, d, —NH—)
EA: shown in Table 2

EXAMPLE 9

[3-Carboxymethyl-5-m-chlorophenylaminomethylidenerhodanine (Compound No. 9)]

The same procedures as in Example 4 except that m-chloroaniline was used instead of allylamine were repeated to give 1.2 g of 3-carboxymethyl-5-m-chlorophenylaminomethylidenerhodanine in the form of yellow crystal by recrystallization from a mixture of acetone and petroleum ether (4/1 by volume) (yield: 73.2%).

The characteristic properties of the product are as follows:
MP: 253° to 255° C. (decomposition)
IR (cm$^{-1}$) 3350 to 2850 (NH, CH), 2650 to 2350 (COOH), 1720 (ring C=O), 1670 (COOH)
MS (m/e): 328 (M+) 284 (M+—COO—)
NMR (ppm): 4.40 (2H, s, —CH$_2$COO), 6.68 to 7.15 (4H, m, aromatic, proton), 7.7 (1H, d, —CH=), 9.9 (1H, d, —NH—)
EA: shown in Table 2

EXAMPLE 10

[3-Carboxymethyl-5-p-bromophenylaminomethylidenerhodanine (Compound No. 10)]

The same procedures as in Example 5 except that p-bromoaniline was used instead of isobutylamine were repeated to give 0.84 g of 3-carboxymethyl-5-p-bromophenylaminomethylidenerhodanine in the form of yellow crystal (yield: 44.0%).

The characteristic properties of the product are as follows:
MP: 264° to 266° C. (decomposition)
IR (cm$^{-1}$): 3350 to 2850 (NH, CH), 2600 to 2350 (COOH), 1730 (ring C=O), 1670 (COOH)
MS (m/e): 373 (M+), 375 (M+ +2)
NMR (ppm): 4.38 (2H, s, —CH$_2$COO—), 6.85 (2H, d, aromatic proton), 7.10 (2H, d, aromatic proton), 7.65 (1H, d, —CH=), 9.90 (1H, broad, —NH—)
EA: shown in Table 2

EXAMPLE 11

[3-Carboxymethyl-5-m-methylphenylaminomethylidenerhodanine (Compound No. 11)]

The same procedures as in Example 5 except that m-toluidine was used instead of isobutylamine to give 1.15 g of 3-carboxymethyl-5-m-methylphenylaminomethylidenerhodanine in the form of yellow crystal by recrystallization from acetone (yield: 74.7%).

The characteristic properties of the product are as follows:
MP: 261° to 263° C. (decomposition)
IR (cm$^{-1}$)3350 to 2850 (NH, CH), 2650 to 2400 (COOH), 1740 (ring C=O), 1680 (COOH)
MS (m/e): 308 (M+)
NMR (ppm): 2.30 (3H, s, —CH$_3$), 4.40 (2H, s, —CH$_2$COO—), 6.60 to 7.20 (4H, m, aromatic proton), 7.70 (1H, d, —CH=), 9.90 (1H, broad, —NH—)
EA: shown in Table 2

Example 12

[3-Carboxymethyl-5-morpholinomethylidenerhodanine (Compound No. 12)]

The same procedures as in Example 5 except that morpholine was used instead of isobutylamine were repeated to give morpholine salt of 3-carboxymethyl-5-morpholinomethylidenerhodanine in the form of light yellow crystal by recrystallization from ethanol.

The characteristic properties of the product are as follows:
MP: 208° to 210° C. (decomposition)
NMR (ppm):

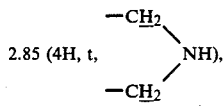

3.30 to 3.60 (12H, m, (—CH$_2$) X 6), 4.20 (2H, s, —CH$_2$COO—), 7.30 (1H, s, —CH=)

The above salt was dissolved into water and the resulting solution was treated in the same manner as in Example 5 to give 0.97 g of 3-carboxymethyl-5-morpholino-methylidenerhodanine in the form of light yellowish red crystal (yield: 67.2 %).

The characteristic properties of the product are as follows:
MP: 293° to 295° C. (decomposition)
IR (cm$^{-1}$): 3150 to 2850 (CH), 2650 to 2400 (COOH), 1720 (ring C=O), 1665 (COOH)
MS (m/e): 288 (M+), 244 (M+—COO)
NMR (ppm): 3.30 to 3.55 (8H, m, (—CH$_2$—) X 4), 4.30 (2H, s, —CH$_2$COO—), 7.30 (1H, s, —CH=)
EA: shown in Table 2

EXAMPLE 13

[3-Carboxymethyl-5-N-methylpiperazinomethylidenerhodanine (Compound No. 13)]

The same procedures as in Example 4 except that N-methylpiperazine was used instead of allylamine were repeated to give 1.1 g of 3-carboxymethyl-5-N-methylpiperazinomethylidenerhodanine in the form of light yellowish red crystal by recrystallization from water (yield: 70.0%).

The characteristic properties of the product are as follows:
MP: 250° to 252° C. (decomposition)
IR (cm$^{-1}$): 3350 to 2850 (CH), 2700 to 2300 (COOH), 1720 (ring C=O), 1670 (COOH)
MS (m/e): 301 (M+)
NMR (ppm): 2.33 (3H, s, CH$_3$—N>),

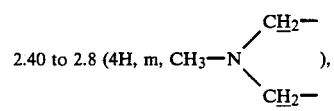

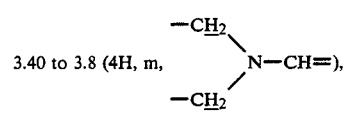

4.30 (2H, s, —CH$_2$COO—), 7.40 (1H, s, —CH=)
EA: shown in Table 2

EXAMPLE 14

[3-Carboxymethyl-5-N-methylhomopiperazinomethylidenerhodanine (Compound No. 14)]

The same procedures as in Example 4 except that N-methylhomopiperazine was used instead of allylamine were repeated to give 1.3 g of 3-carboxymethyl-5-N-methylhomopiperazinomethylidenerhodanine in the form of light brown powder by recrystallization from a mixture of dimethylsulfoxide and water (9/1 by volume) (yield: 82.3%)

The characteristic properties of the product are as follows:
MP: 244° to 246° C. (decomposition)
IR (cm$^{-1}$): 3350 to 2850 (CH), 2700 to 2300 (COOH), 1725 (ring C=O), 1670 (COOH)
MS (m/e): 315 (M+)
NMR (ppm):

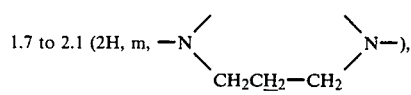

1.7 to 2.1 (2H, m, $-N\begin{array}{c}\diagup\\\diagdown\end{array}CH_2CH_2-CH_2\begin{array}{c}\diagdown\\\diagup\end{array}N-$), 2.33 (3H, s, CH$_3$—N<),

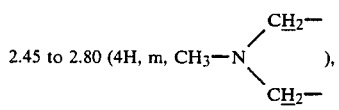

2.45 to 2.80 (4H, m, CH$_3$—N$<$CH$_2-$ / CH$_2-$),

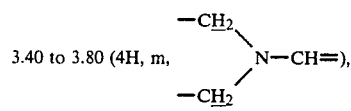

3.40 to 3.80 (4H, m, —CH$_2$ / —CH$_2$ $\diagdown$ N—CH=), 4.35 (2H, s, —CH$_2$COO—), 7.45 (1H, s, —CH=)
EA: shown in Table 2

EXAMPLE 15

[3-Carboxymethyl-5-(2-biphenylyl)aminomethylidenerhodanine (Compound No. 15)]

The same procedures as in Example 4 except that o-phenylaniline was used instead of allylamine and the reaction was conducted at a room temperature for 4 to 20 hours to give 1.36 g of 3-carboxymethyl-5-(2biphenylyl)aminomethylidenerhodanine in the form of yellow crystal (yield: 71.5%).

The characteristic properties of the product are as follows:
MP: 248° to 250° C. (decomposition)
IR (cm$^{-1}$) 3300 to 2850 (NH, CH), 2650 to 2350 (COOH), 1735 (ring C=O), 1660 (COOH)
MS (m/e): 370 (M+)

NMR (ppm): 4.40 (2H, s, —CH$_2$COO—), 6.95 to 7.40 (9H, m, aromatic proton), 7.55 (1H, d, —CH=), 9.80 (1H, d, —NH—)
EA: shown in Table 2

Example 16

[3-Carboxymethyl-5-m-methoxyphenylaminomethylidenerhodanine sodium salt (sodium salt of Compound No. 7)]

129.6 milligrams (0.0004 mole) of 3-carboxymethyl-5-m-methoxyphenylaminomethylidenerhodanine prepared in Example 7 was dissolved in 4 ml of 0.1N sodium hydroxide and the resulting solution was freeze-dried to quantitively give the desired compound in the form of yellow powder.
MP: 268° to 270° C. (decomposition)
Sodium salts of Compound Nos. 1 to 2, Nos. 4 to 6 and Nos. 8 to 15 were obtained in the same manner as described above.

EXAMPLE 17

[3-Carboxymethyl-5-m-methoxyphenylaminomethylidenerhodanine potassium salt (potassium salt of Compound No. 7)]

129.6 milligrams (0.0004 mole) of 3-carboxymethyl-5-m-methoxyphenylaminomethylidene rhodanine was dissolved in 4 ml of 0.1N potassium hydroxide and the resulting solution was freeze-dried to quantitatively give the desired compound in the form of red powder.
MP: 280° to 282° C. (decomposition)
Potassium salts of Compound Nos. 1 to 2, Nos. 4 to 6 and Nos. 8 to 15 were obtained in the same manner as described above.

TABLE 2

| Compound No. | Molecular formula | Molecular weight | Calcd. (%) C | H | N | Found (%) C | H | N |
|---|---|---|---|---|---|---|---|---|
| 1 | $C_7H_8N_2O_3S_2$ | 232.282 | 36.20 | 3.47 | 12.6 | 36.39 | 3.72 | 12.33 |
| 2 | $C_8H_{10}N_2O_3S_2$ | 246.309 | 39.01 | 4.09 | 11.37 | 38.96 | 4.28 | 11.29 |
| 3 | $C_8H_{10}N_2O_4S_2 \cdot$ HOCH$_2$CH$_2$NH$_2$ | 323.393 | 37.14 | 5.30 | 13.00 | 36.92 | 5.46 | 13.26 |
| 4 | $C_9H_{10}N_2O_3S_2$ | 258.320 | 41.85 | 3.90 | 10.84 | 41.78 | 3.81 | 11.03 |
| 5 | $C_{10}H_{14}N_2O_3S_2$ | 274.364 | 43.78 | 5.14 | 10.21 | 43.57 | 4.97 | 10.36 |
| 6 | $C_{12}H_{18}N_2O_3S_2$ | 302.418 | 47.66 | 6.00 | 9.26 | 47.52 | 5.79 | 9.42 |
| 7 | $C_{13}H_{12}N_2O_4S_2$ | 324.380 | 48.14 | 3.73 | 8.64 | 48.35 | 3.72 | 8.50 |
| 8 | $C_{13}H_{12}N_2O_4S_2$ | 324.380 | 48.14 | 3.73 | 8.64 | 47.99 | 3.73 | 8.44 |
| 9 | $C_{12}H_9N_2O_3S_2Cl$ | 328.799 | 43.84 | 2.76 | 8.52 | 43.63 | 2.70 | 8.26 |
| 10 | $C_{12}H_9N_2O_3S_2Br$ | 373.255 | 38.62 | 2.43 | 7.51 | 38.57 | 2.38 | 7.67 |
| 11 | $C_{13}H_{12}N_2O_3S_2$ | 308.381 | 50.63 | 3.92 | 9.08 | 50.64 | 3.98 | 8.91 |
| 12 | $C_{10}H_{12}N_2O_4S_2$ | 288.347 | 41.66 | 4.19 | 9.72 | 41.91 | 4.34 | 9.63 |
| 13 | $C_{11}H_{15}N_3O_3S_2$ | 301.389 | 43.84 | 5.02 | 13.94 | 43.63 | 5.14 | 14.03 |
| 14 | $C_{12}H_{17}N_3O_3S_2$ | 315.416 | 45.70 | 5.43 | 13.32 | 45.55 | 5.15 | 13.12 |
| 15 | $C_{18}H_{14}N_2O_3S_2$ | 370.453 | 58.36 | 3.81 | 7.56 | 58.29 | 3.77 | 7.80 |

EXAMPLE 18

A mixture of 10 parts by weight of 3-carboxymethyl-5-m-methoxyphenylaminomethylidenerhodanine (Compound No. 7), 30 parts of lactose, 45 parts by weight of corn starch, 15 parts by weight of a microcrystalline cellulose (commercially available under the registered trade mark "Avicel" made by Asahi Chemical Industry Co., Ltd.), 3 parts by weight of methyl cellulose and 2 parts by weight of magensium stearate was thoroughly blended and then screened through a 50 mesh screen. The resulting powder was tabletted by an automatic tabletting machine to give tablets containing 20 mg of the essential active ingredient per one tablet.

EXAMPLE 19

A mixture of 10 parts by weight of 3-carboxymethyl-5-m-chlorophenylaminomethylidenerhodanine (Compound No. 9), 55 parts by weight of lactose, 30 parts by weight of corn starch, 8 parts by weight of Avicel and 2 parts by weight of magnesium stearate was thoroughly blended. The mixture was then filled in capsules made of gelatin to give capsules containing 20 mg of the essential active ingredient per one capsule.

EXAMPLE 20

The tablets obtained in Example 18 were pulverized and the resulting powder was screened through a 50 mesh screen and a 100 mesh screen to give granules having a particle size of 5 to 100 meshes and containing 50 mg of the essential active ingredient per 1 g of granules.

EXAMPLE 21

The same mixture used in Example 19 was finely pulverized and then screened through a 100 mesh screen to give a powder having an average particle size of 100 meshes and containing 50 mg of the essential active ingredient per 1 g of powder.

EXAMPLE 22

[Platelet aggregation inhibiting activity]

The platelet aggregation inhibiting activity was examined with the rhodanine derivatives (I) of the present invention.

Test method

Blood samples were collected from the auricular blood vessel of albino rabbits (white local breed), and washed platelets were prepared therefrom by the method of Baenziger et al. [N. L. Baenziger and P. W. Majerus, Methods in Enzymology, 31, 149 to 155 (1974)]. The platelets were suspended in a 15 mM Tris-hydrochloric acid buffer in a final concentration of $6 \times 10^8$ cells/ml (Tris: tris(hydroxymethyl)aminomethane). Each test compound was added thereto and incubation was carried out at 37° C. for 2 minutes. Then, the platelets were stimulated by addition of thrombin (final concentration 0.2 unit/ml; made by Mochida Pharmaceutical Co.) and the aggregation inhibiting activity was estimated by observation of the aggregation reaction using an aggregometer (made by Briston Co.).

The results obtained are shown in Table 3 in terms of $IC_{50}$ (50 % inhibition concentration in M).

TABLE 3

| Compound No. | $IC_{50}$ (M) |
| --- | --- |
| 7 | $3.1 \times 10^{-4}$ |
| 8 | $3.1 \times 10^{-4}$ |
| 9 | $3.0 \times 10^{-4}$ |
| 10 | $3.0 \times 10^{-4}$ |
| 11 | $3.2 \times 10^{-4}$ |
| 15 | $4.1 \times 10^{-4}$ |
| Dipyridamole | $2.0 \times 10^{-4}$ |

As shown in Table 3, Compound Nos. 7, 8, 9, 10 and 11 inhibited the thrombin-induced aggregation of washed rabbit platelets by 50% at a concentration of $3 \times 10^{-4}$ M. With other compounds, too, platelet aggregation inhibiting activity was observed, though it was weaker than that of the above five compounds. The above five compounds were almost comparable in said activity to Dipyridamole, a platelet aggretation inhibitor in wide use.

EXAMPLE 23

[Aldose reductase inhibiting activity]

The aldose reductase inhibiting activity was examined with respect to the rhodanine derivative (I) of the present invention.

Test Method

The test was carried out according to the method of Hayman et al. [S. Hayman and J. H. Kinoshita, J. Biol. Chem., 240, 877 to 882 (1965)].

Thus, Wistar strain male rats were sacrificed by decapitation, the lenses were excised and homogenized with a 0.1 M phosphate buffer [pH 6.8; containing 1 mM of mercaptoethanol and 1 mM of nicotinamide-adenine dinucleotide phosphate (NADP)]. The homogenate was then centrifuged at 10,000 g for 15 minutes and the supernatant was used as the crude enzyme solution.

Separately, a 0.1M phosphate buffer (pH 6.2) containing 0.104 mM of NADPH (reduced form of NADP) and 10 mM of DL-glyceraldehyde was prepared. To this buffer solution, there was added 15 μl of each of solutions of each test compound in varied concentrations, followed by addition of 25 μl of the crude enzyme solution prepared in advance, to thereby initiate the reaction. The decrease in absorbance at 340 nm was measured using a high-sensitivity self-registering spectrophotometer (Model SM-401 made by Union Giken Kabushiki Kaisha).

The results obtained are shown in Table 4 in term of $IC_{50}$ (50% inhibition concentration in M).

TABLE 4

| Compound No. | $IC_{50}$ (M) |
| --- | --- |
| 1 | $1.3 \times 10^{-6}$ |
| 2 | $6.5 \times 10^{-7}$ |
| 3 | $7.0 \times 10^{-7}$ |
| 4 | $3.0 \times 10^{-7}$ |
| 5 | $6.0 \times 10^{-7}$ |
| 6 | $2.8 \times 10^{-7}$ |
| 7 | $2.6 \times 10^{-8}$ |
| 8 | $5.0 \times 10^{-8}$ |
| 9 | $2.3 \times 10^{-8}$ |
| 10 | $5.0 \times 10^{-8}$ |
| 11 | $3.6 \times 10^{-8}$ |
| 12 | $3.4 \times 10^{-7}$ |
| 13 | $2.0 \times 10^{-7}$ |
| 14 | $1.3 \times 10^{-6}$ |
| 15 | $1.5 \times 10^{-7}$ |
| Sorvinyl (Note) | $2.0 \times 10^{-7}$ |

Note: the registered trademark of S—6-fluorospiro(chroman-4,4'-imidazolidine)-2',5'-dione having the following formula:

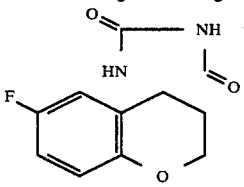

(made by Pfizer Inc.)

In the laboratory test for inhibitory activity against aldose reductase obtained from the rat eye lens, all the compounds listed in Table 4 showed 50% inhibition within the concentration range of $10^{-8}$ to $10^{-6}$ M.

EXAMPLE 24

[Acute toxicity]

The acute toxicity in mice was examined with the rhodanine derivative (I) of the present invention.

Test Methed

To groups of 4 male ddY strain mice (5 weeks of age) were orally administered by gavage each test compound suspended in a 10% gum arabic and the mice were observed for death or survival for 2 weeks.

The results obtained with respect to Compound Nos. 7, 9, 11 and 15 are shown in Table 5.

TABLE 5

| Oral dose (g/kg body weight) | Rate of death (%) |
| --- | --- |
| 1.0 | 0 |
| 2.0 | 0 |
| 4.0 | 0 |

As shown in Table 5, with respect to Compound Nos. 7, 9, 11 and 15, no deaths were noted up to a dose of 4 g/kg body weight, and therefore the $LD_{50}$ value (oral) for each compound was greater than 4 g/kg body weight.

It was thus demonstrated that the rhodanine derivatives (I) of the present invention are of very low toxicity.

As above results indicate, the rhodanine derivatives (I) of the present invention can be used as novel and highly safe therapeutic agents for diabetic complications which have not only potent platelet aggregation inhibiting activity but also aldose reductase inhibiting activity much more potent as compared with the known compounds having aldose reductase inhibiting activity.

In addition to the ingredients used in the Examples, other ingredients can be used in the Examples as set forth in the specification to obtain susbtantially the same results.

What we claimed is:

1. A rhodanine compound having the following formula (I):

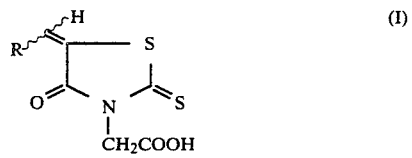

wherein R is 2-biphenylylamino, 3-methoxyphenylamino, 2-methoxyphenylamino, 3chlorophenylamino, 4-bromophenylamino, or m-tolylamino; or a nontoxic salt thereof.

2. A pharmaceutical composition as a therapeutic agent for diabetic complications which comprises as an essential active ingredient an effective amount of a rhodanine compound having the following formula (I):

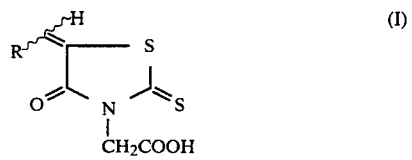

wherein R is 2-biphenylylamino, 3-methoxyphenylamino, 2-methoxyphenylamino, 3-chlorophenylamino, 4-bromophenylamino, or m-tolylamino; or a nontoxic salt thereof.

* * * * *